(12) United States Patent  
Lane

(10) Patent No.: US 8,768,481 B2
(45) Date of Patent: Jul. 1, 2014

(54) METHODS TO AVOID FREQUENCY LOCKING IN A MULTI-CHANNEL NEUROSTIMULATION SYSTEM USING A GREATEST COMMON DIVISOR RULE

(75) Inventor: Courtney Lane, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1150 days.

(21) Appl. No.: 12/550,185

(22) Filed: Aug. 28, 2009

(65) Prior Publication Data

US 2011/0054570 A1    Mar. 3, 2011

(51) Int. Cl.
*A61N 1/00* (2006.01)

(52) U.S. Cl.
USPC .......................................................... 607/60

(58) Field of Classification Search
USPC ......... 607/60, 30, 32, 59, 66, 70, 72; 128/903
See application file for complete search history.

(56) References Cited

U.S. PATENT DOCUMENTS

| | | | |
|---|---|---|---|
| 5,354,319 A * | 10/1994 | Wyborny et al. | ............... 607/32 |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 2004/0098063 A1 | 5/2004 | Goetz | |
| 2008/0319509 A1 | 12/2008 | Laback et al. | |

FOREIGN PATENT DOCUMENTS

| | | |
|---|---|---|
| EP | 0042924 A2 | 1/1982 |
| GB | 1123241 | 8/1968 |
| WO | WO 2009/137121 A1 | 11/2009 |

OTHER PUBLICATIONS

PCT International Preliminary Report on Patentability (Chapter I of the Patent Cooperation Treaty) for PCT/US2010/047037, Applicant: Boston Scientific Neuromodulation Corporation, Form PCT/IB/326 and 373, dated Mar. 8, 2012 (7pages).
PCT International Search Report for PCT/US2010/047037, Applicant: Boston Scientific Neuromodulation Corporation, Form PCT/ISA/210 and 220, dated Nov. 4, 2010 (8 pages).
PCT Written Opinion of the International Search Authority for PCT/US2010/047037, Applicant: Boston Scientific Neuromodulation Corporation, Form PCT/ISA/237, dated Nov. 4, 2010 (7 pages).

* cited by examiner

*Primary Examiner* — Eric D. Bertram
*Assistant Examiner* — Elizabeth K So
(74) *Attorney, Agent, or Firm* — Vista IP Law Group LLP

(57) ABSTRACT

A method and external control device for preventing frequency locking in a multi-channel neurostimulation system and external control device is provided. A plurality of pulsed electrical waveforms is provided. Each of the pulsed electrical waveforms has a period and a pulse width. The greatest common divisor of the periods of the pulsed electrical waveforms is computed, and the sum of the pulse widths of the pulsed electrical waveforms is computed. A plurality of timing channels in the neurostimulation system is allowed to be programmed with the pulsed electrical waveforms if the greatest common divisor is equal to or greater than the sum.

21 Claims, 9 Drawing Sheets

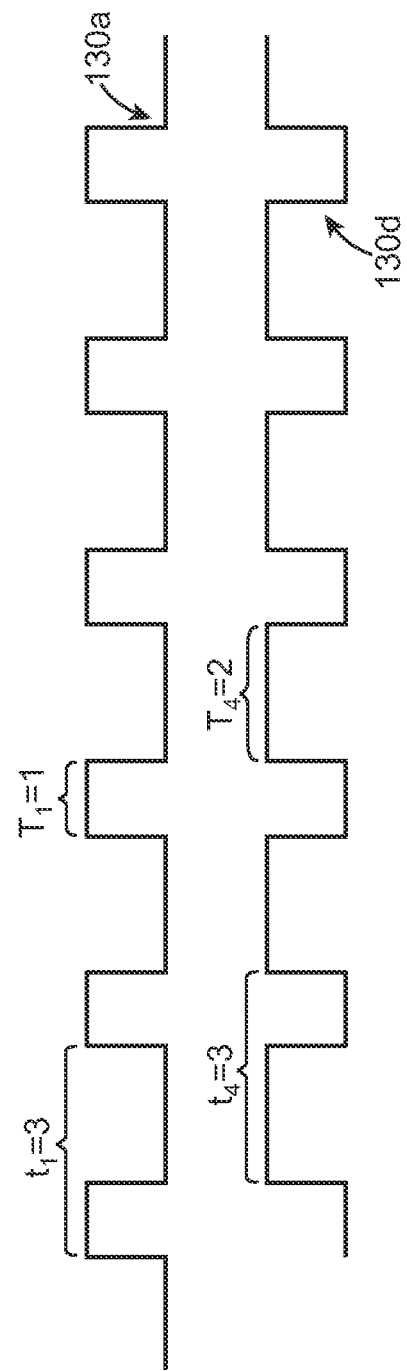

METHODS TO AVOID FREQUENCY LOCKING IN A MULTI-CHANNEL NEUROSTIMULATION SYSTEM USING A GREATEST COMMON DIVISOR RULE

FIELD OF THE INVENTION

The present invention relates to tissue stimulation systems, and more particularly, to a system and method for eliminating or reducing frequency locking in multi-channel neurostimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. However, the number of electrodes available combined with the ability to generate a variety of complex stimulation pulses, presents a vast selection of stimulation parameter sets to the clinician or patient.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Often, multiple timing channels are used when applying electrical stimulation to target different tissue regions in a patient. For example, in the context of SCS, the patient may simultaneously experience pain in different regions (such as the lower back, left arm, and right leg) that would require the electrical stimulation of different spinal cord tissue regions. In the context of DBS, a multitude of brain structures may need to be electrically stimulated in order to simultaneously treat ailments associated with these brain structures. Each timing channel identifies the combination of electrodes used to deliver electrical pulses to the targeted tissue, as well as the characteristics of the current (pulse amplitude, pulse duration, pulse frequency, etc.) flowing through the electrodes.

The use of multiple timing channels can often lead to problems with the electrical stimulation systems due to the potential of an overlap in pulses between two or more timing channels. Overlapping of pulses using a common electrode can make neurostimulation systems ineffective or even harmful. Current neurostimulation systems employing multiple timing channels use a method known as the "token" method to prevent overlap of pulses. This method allows an electrical pulse to be transmitted in the timing channel with the "token," while the other timing channels wait their turn. Then, the "token" is passed to the next timing channel. However, if the stimulation trains of the channels overlap, such that they need the "token" at the same time, transmission of an electrical pulse within the second channel must wait until the end of the transmission of the electrical pulse in the first timing channel. One possible result is that the frequency of the electrical pulses transmitted in the second timing channel gets "locked" to (i.e. matches) the frequency of the electrical pulses transmitted in the first timing channel; alternatively, one can get galloping or clumping of electrical pulses. Therefore, when the occurrence of stimulation pulses is pushed out in time, stimulation therapy becomes ineffective or even harmful for tissue regions that require stimulation at specific, regular frequencies.

The "token" method may best be understood with reference to FIG. 1. As there shown, a first electrical pulsed waveform 5a having a first frequency is transmitted within timing channel A, and a second electrical pulsed waveform 5b having a second frequency is desired to be transmitted within timing channel B. Because timing channel A has the "token," the pulses of the second electrical pulsed waveform 5b that are to be transmitted in timing channel B must be "bumped" each time they overlap with the pulses of the first electrical pulsed waveform 5a. As can be seen in the bumped electrical pulsed waveform 5c, when a pulse is bumped (shown by the horizontal arrows), the next pulse relies on the new (bumped) pulse for timing. Thus, the next pulse is "double bumped": once when the previous pulse is bumped and a second time when it overlaps a pulse of the pulsed electrical waveform 5a transmitting during timing channel A. As a result, the frequency of the pulses in the second electrical pulsed waveform 5b is forced (i.e., locked) into the frequency for the first electrical pulsed waveform 5a, resulting in a pulsed electrical waveform 5d that has a frequency twice as small as the desired frequency.

There, thus, remains a need to provide an improved method for preventing or minimizing the overlap of pulses within multi-channel neurostimulation systems.

SUMMARY OF THE INVENTION

In accordance with one aspect of the present inventions, a method for preventing overlapping pulses in a multi-channel neurostimulation system is provided. The method comprises defining a plurality of pulsed electrical waveforms, each of the pulsed electrical waveforms having a period and a pulse width. The pulsed electrical waveform may, e.g., be defined in response to a user input. The method further comprises computing the greatest common divisor of the periods of the pulsed electrical waveforms, and computing the sum of the pulse widths of the pulsed electrical waveforms. The method further comprises allowing a plurality of timing channels in the neurostimulation system to be programmed (e.g., with an external control device) with the pulsed electrical waveforms if the greatest common divisor is equal to or greater than the sum. The timing channels may be programmed in a manner, such that no pulse temporally overlaps another pulse.

In one method, at least two of the timing channels have been programmed with a common electrode and the time periods for the electrical pulsed waveforms are different. The method may further comprise delivering stimulation energy from the neurostimulation system in accordance with the programmed pulsed electrical waveforms to provide therapy to a patient; for example, to stimulate different tissue regions of the patient. The method may optionally comprise interleaving two or more pulsed electrical waveforms into a single pulsed waveform, in which case, the plurality of electrical pulsed waveforms will include the single pulsed waveform, and two or more of the timing channels are allowed to be respectively programmed with the two or more pulsed waveforms. For example, if the time periods for the two or more pulsed electrical waveforms are equal, they may be interleaved into the single pulsed waveform.

In accordance with a second aspect of the present inventions, an external control device for a neurostimulation device is provided. The external control device comprises a user interface configured for receiving an input from a user, telemetry circuitry, and a processor configured for defining a plurality of pulsed electrical waveforms in response to the input from the user. The pulsed electrical waveform may, e.g., be defined in response to a user input. The processor is further configured for computing the greatest common divisor of the periods of the pulsed electrical waveforms, and computing the sum of the pulse widths of the pulsed electrical waveforms. The processor is further configured for programming via the telemetry circuitry a plurality of timing channels in the neurostimulation device with the pulsed electrical waveforms if the greatest common divisor is equal to or greater than the sum. The timing channels may be programmed in a manner, such that no pulse temporally overlaps another pulse.

In one embodiment, at least two of the timing channels have been programmed with a common electrode and the time periods for the electrical pulsed waveforms are different. In an optional embodiment, the processor is further configured for interleaving two or more pulsed electrical waveforms into a single pulsed waveform, wherein the plurality of electrical pulsed waveforms includes the single pulsed waveform, in which case, the plurality of electrical pulsed waveforms will include the single pulsed waveform, and two or more of the timing channels are allowed to be respectively programmed with the two or more pulsed waveforms. For example, if the time periods for the two or more pulsed electrical waveforms are equal, they may be interleaved into the single pulsed waveform. In one embodiment, the processor is configured for programming the timing channels, such that stimulation energy is delivered from the neurostimulation device in accordance with the programmed pulsed electrical waveforms to provide therapy to a patient. For example, different tissue regions of the patient can be stimulated respectively with delivered stimulation energy.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 12 is a timing diagram illustrating two of the electrical pulsed waveforms combined into a single electrical pulsed waveform by the SCS system of FIG. 2.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
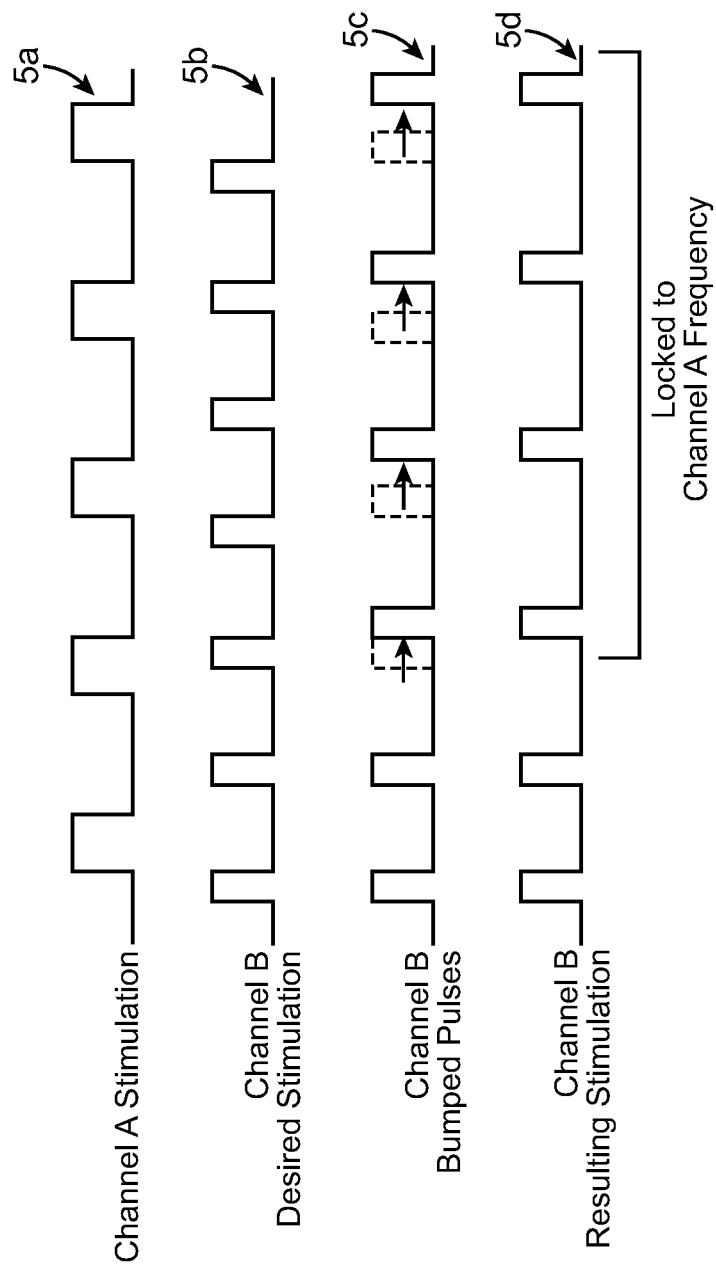
FIG. 1 is timing diagram illustrating a prior art technique for preventing the overlap between pulses of electrical pulsed waveforms programmed in multiple timing channels.
Figure 2:
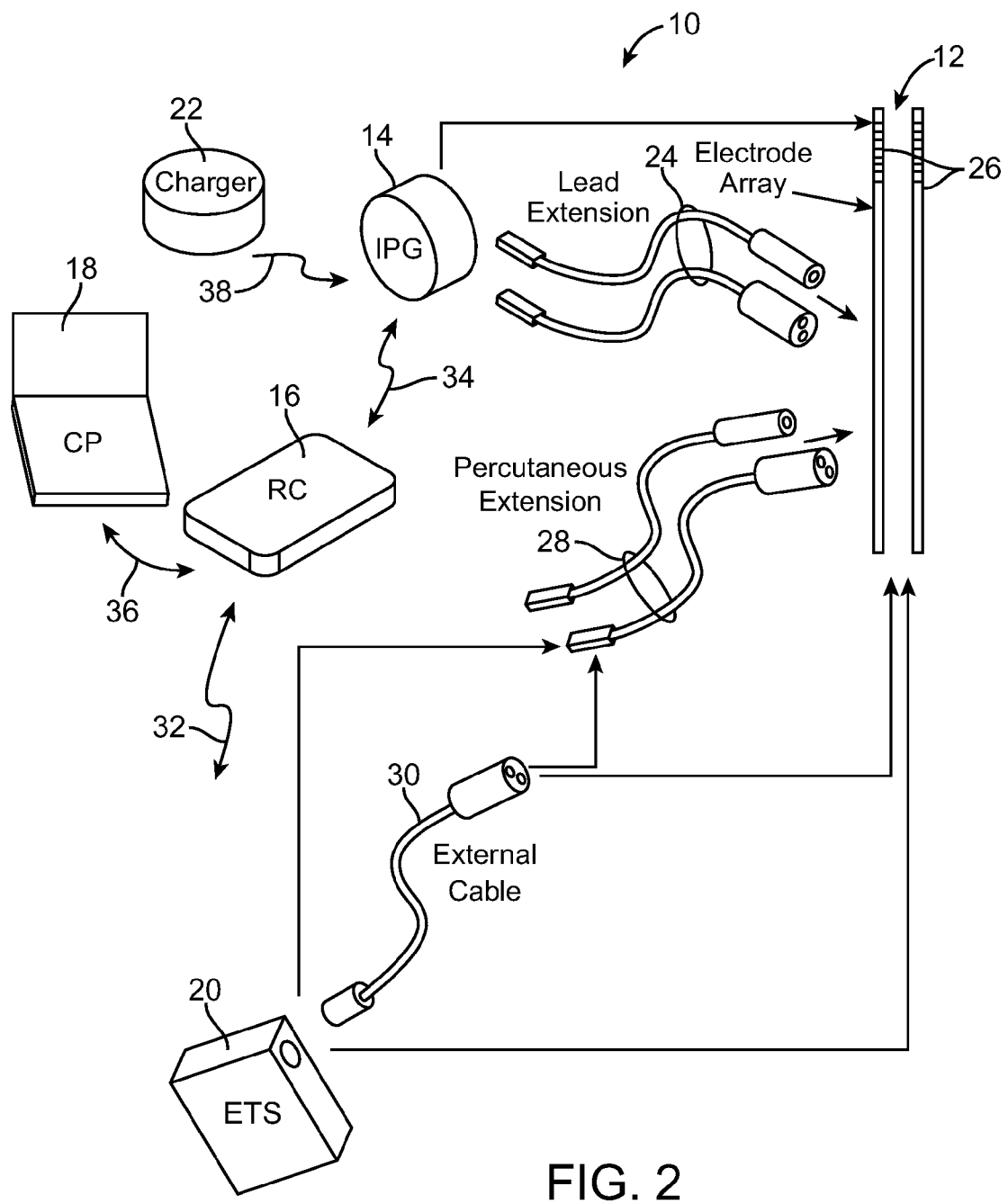
FIG. 2 is a plan view of an embodiment of a spinal cord stimulation (SCS) system arranged in accordance with the present inventions.

Turning first to FIG. 2, an exemplary SCS neurostimulation system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 may be arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 3:
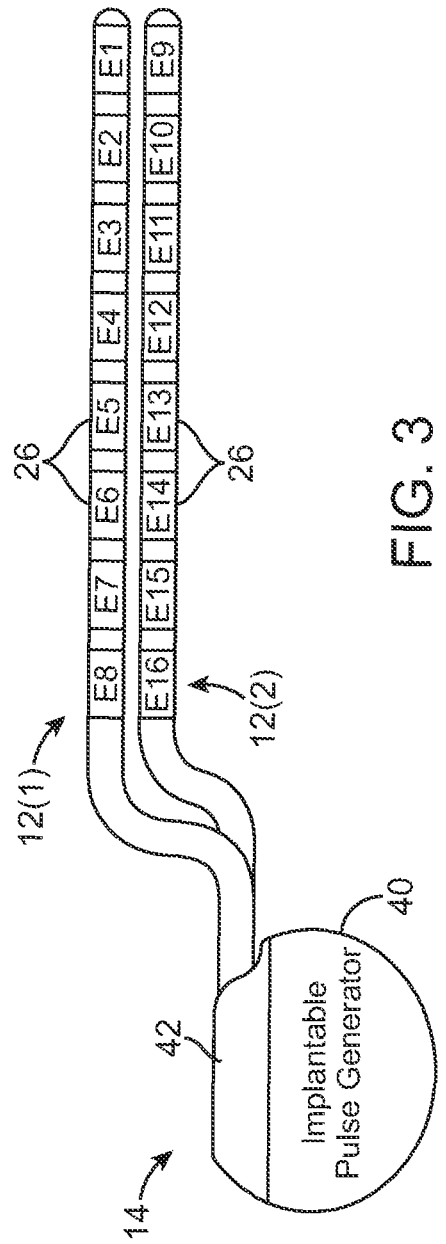
FIG. 3 is a profile view of an implantable pulse generator (IPG) and percutaneous leads used in the SCS system of FIG. 2.

Referring now to FIG. 3, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(1) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse). The recharge can be active (i.e. energy is expended to reverse the current) or passive (i.e. the circuit is allowed to reverse the current by connecting the circuit together in such a way that the built-up charge is discharged through the circuit).

In the illustrated embodiment, the IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the electric neurostimulation system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
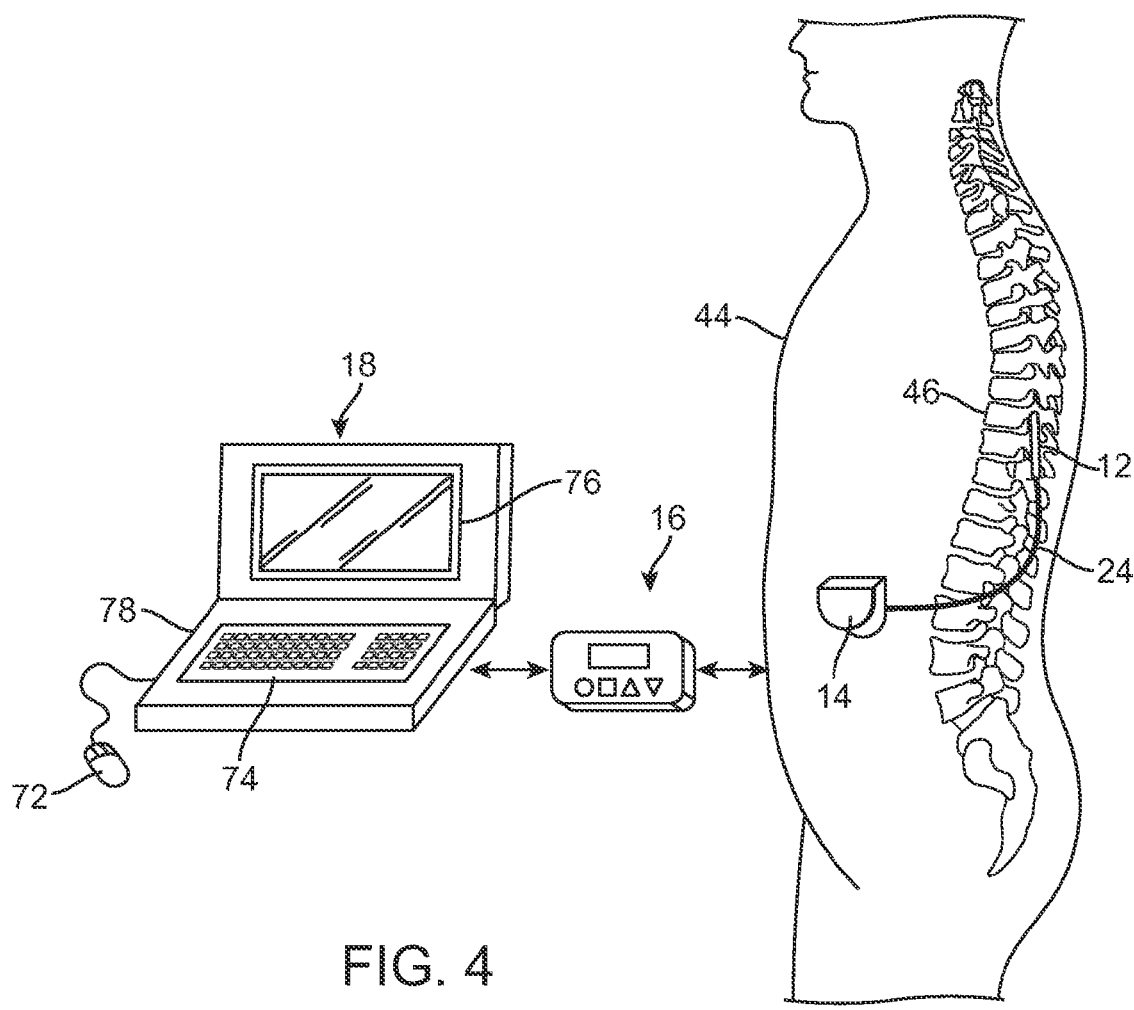
FIG. 4 is a plan view of the SCS system of FIG. 2 in use with a patient.

As shown in FIG. 4, the electrode leads 12 are implanted within the spinal column 46 of a patient 44. The preferred placement of the electrode leads 12 is adjacent, i.e., resting upon, the dura near the spinal cord area to be stimulated. Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 5:
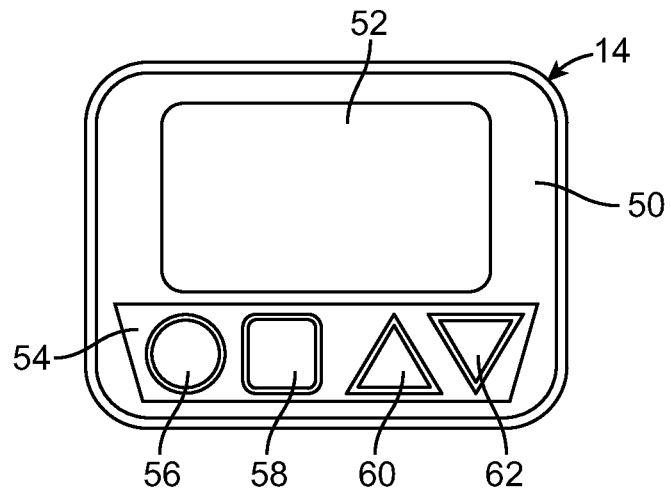
FIG. 5 is a plan view of a remote control that can be used in the SCS system of FIG. 2.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
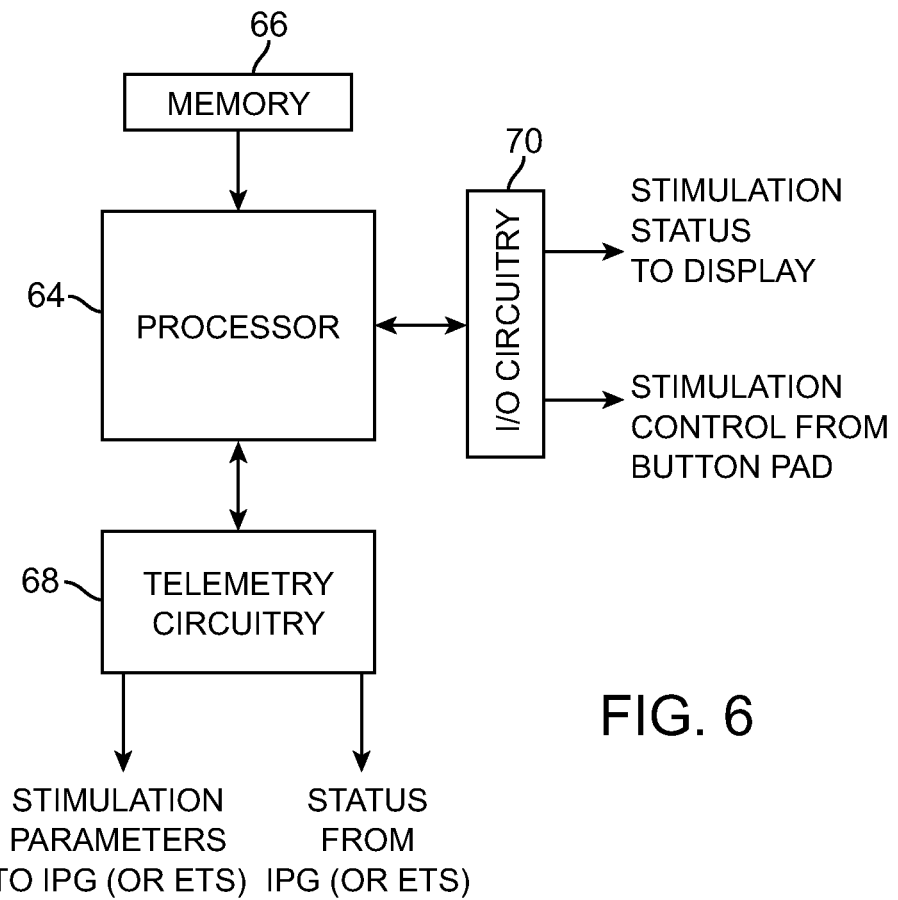
FIG. 6 is a block diagram of the internal componentry of the remote control of FIG. 5.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, the processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26.

As shown in FIG. 4, the overall appearance of the CP 18 may be that of a laptop personal computer (PC), and in fact, may be implemented, using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 7:
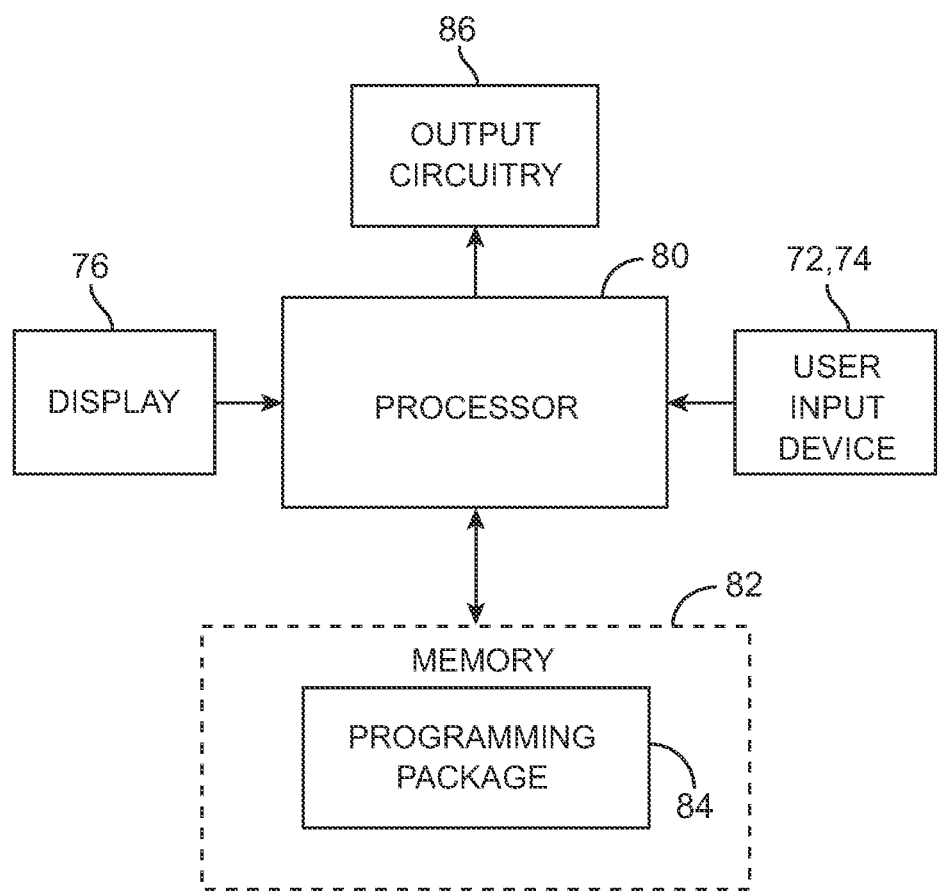
FIG. 7 is a block diagram of the components of a clinician's programmer that can be used in the SCS system of FIG. 2.

To allow the clinician to perform these functions, the CP 18 includes a mouse 72, a keyboard 74, and a programming display screen 76 housed in a case 78. It is to be understood that in addition to, or in lieu of, the mouse 72, other directional programming devices may be used, such as a joystick, or directional keys included as part of the keys associated with the keyboard 74. As shown in FIG. 7, the CP 18 generally includes a processor 80 (e.g., a central processor unit (CPU)) and memory 82 that stores a stimulation programming package 84, which can be executed by the processor 80 to allow a clinician to program the IPG 14 and RC 16. As well as controlling other functions of the CP 18, including any computation and determination functions described in further detail below, the processor 80 generates new stimulation parameter sets in response to the user operation of the user input devices 72, 74. These new stimulation parameter sets, under proper circumstances discussed below, would then be transmitted to the IPG 14 (or EPS 20) and RC 16 via the telemetry circuitry 68.

Significantly, the IPG 14 may be programmed by the CP 18 (or alternatively the RC 16) to operate over multiple timing channels. In particular, any combination of electrodes may be assigned to up to k possible groups, i.e., timing channels. In one embodiment, k may equal four. The timing channel identifies which electrodes are selected to synchronously source or sink current to create an electric field in the tissue to be stimulated. The programming software in the CP 18 may be used to set stimulation parameters including electrode polarity, amplitude, pulse rate and pulse width for the electrodes of a given timing channel, among other possible programmable features.

The electrode combinations assigned to the respective timing channels may be completely different from each other or can have one or more common electrodes. If one or more common electrodes are assigned to the timing channels, including the case, as discussed in the background, it is desirable to prevent overlap between the electrical pulses generated in the respective timing channels. The CP 18 is capable of eliminating overlapping stimulation pulses between the timing channels by allowing the user to only program multiple timing channels of the IPG 14 with pulsed electrical waveforms that can be interleaved in a manner that does not require "bumping" of any pulses.

Figure 8:
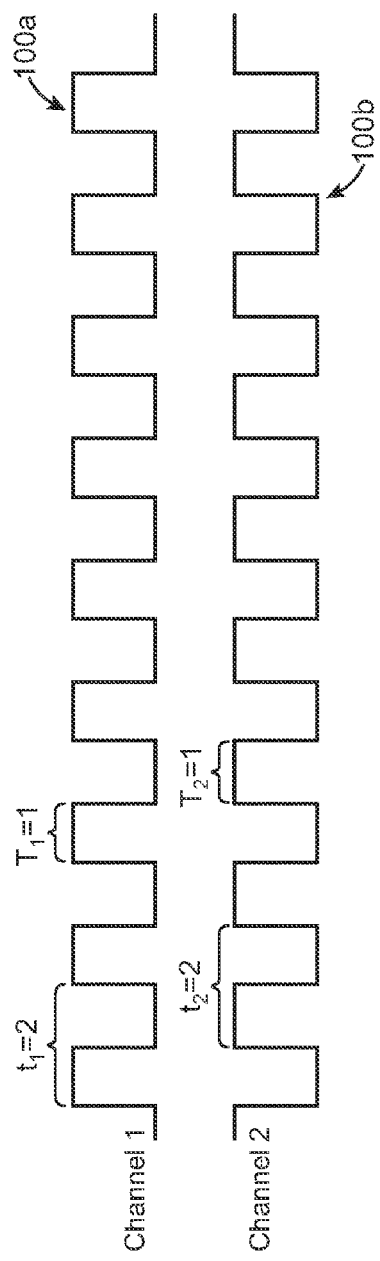
FIG. 8 is a timing diagram illustrating two timing channels that are programmed with a first set of electrical pulsed waveforms by the SCS system of FIG. 2.

In particular, and with reference to FIG. 8, two timing channels (Channel 1 and Channel 2) of the IPG 14 may potentially be programmed by the CP 18 with two electrical pulsed waveforms 100a, 100b, respectively. The electrode combinations assigned to the respective timing channels will typically be those that result in the treatment of two different regions (e.g., in the case of SCS, lower back and left arm). As briefly discussed above, each timing channel identifies the electrodes that are selected to synchronously source or sink current to create an electrical field in the tissue to be stimulated, and that the amplitude and polarities of electrodes assigned to each timing channel may vary. Thus, there may be more than one pulsed electrical waveform delivered within any particular timing channel, such as those exemplified in U.S. Pat. No. 6,895,280, which is expressly incorporated herein by reference. For purposes of brevity and clarity, however, only one pulsed electrical waveform is shown for each timing channel. Furthermore, electrical pulsed waveforms illustrated in FIG. 8 are monophasic in nature, although the electrical pulsed waveforms delivered during a timing channel can be multiphasic in nature.

As discussed above, the CP 18 may indirectly program the IPG 14 via the RC 16. The first electrical pulsed waveform 100a has a time period $t_1$ and a pulse width $T_1$, and the second electrical pulsed waveform 100b has a time period $t_2$ and a pulse width $T_2$. These electrical pulsed waveforms 100a, 100b may be defined in response to an input received by the user interface (mouse 72 or keyboard 74) of the CP 18 in a conventional manner. Stimulation energy can then be delivered from the IPG 14 over the multiple timing channels to in accordance with the programmed pulsed electrical waveforms 100a, 100b to provide therapy to the patient (e.g., by stimulating different tissue regions of the patient respectively with the programmed pulsed electrical waveforms 100a, 100b).

The CP 18 can determine whether the electrical pulsed waveforms 100a, 100b can be interleaved in a manner that does not require bumping of any pulses (thereby preventing frequency locking or other issues between the timing channels) based on function of the greatest common divisor (GCD) of the time periods $t_1$, $t_2$ and the sum of the pulse widths $T_1$, $T_2$ of the respective electrical pulsed waveforms 100. In particular, if $GCD(t_1, t_2) \geq T_1 + T_2$, it is determined that the electrical pulsed waveforms 100a, 100b can be interleaved without the need to bump pulses to prevent pulse overlap. To this end, the CP 18 computes the GCD of the time periods $t_1$, $t_2$ and the sum of the pulse widths $T_1$, $T_2$, and allows the timing channels to be programmed with the pulsed electrical waveforms 100a, 100b if the GCD of the time periods $t_1$, $t_2$ is equal to or greater than the sum of the pulse widths $T_1$, $T_2$. The CP 18 may program the timing channels of the IPG 14 simply by interleaving the electrical pulsed waveforms 100a, 100b, such that no pulses in the waveforms 100a, 100b temporally overlap each other.

In the illustrated embodiment, the time period $t_1$ has a unit value of 2, the time period $t_2$ has a unit value of 2, the pulse width $T_1$ has a unit value of 1, and the pulse width $T_2$ has a unit value of 1. In this case, $GCD(t_1, t_2) \geq T_1+T_2$ becomes $GCD(2, 2) \geq 1+1$, which becomes $2 \geq 2$. Thus, the electrical pulsed waveforms 100a, 100b can be interleaved in a manner without the need to bump pulses to prevent pulse overlap. As such, the CP 18 allows the user to program the timing channels of the IPG 14 with the electrical pulsed waveforms 100a, 100b. It can be appreciated from FIG. 8 that if two electrical pulsed waveforms have the same time period and same pulse width, the waveforms can be interleaved without requiring the pulses to be bumped to prevent overlap. Additionally, it can be appreciated that if one of the pulses has a shorter pulsewidth and the other has a larger pulsewidth, the two pulses can still fit without overlapping.

However, this technique can also be applied to electrical pulsed waveforms that have different time periods. For example, with reference to FIG. 9, two timing channels (Channel 1 and Channel 2) of the IPG 14 may potentially be programmed by the CP 18 with two electrical pulsed waveforms 110a, 110b, which are similar to the electrical pulsed waveforms 100a, 100b illustrated in FIG. 8, with the exception that the time periods $T_1$, $T_2$ of the waveforms 110a, 110b differ from each other, while the pulse widths $t_1$, $t_2$ of the waveforms 100a, 100b remain the same. In this example, some of the pulses in the electrical pulsed waveforms 100a, 100b illustrated in FIG. 8 have been dropped to define the electrical pulsed waveforms 110a (every other one), 110b (the second and third of every three pulses) illustrated in FIG. 9.

Figure 9:
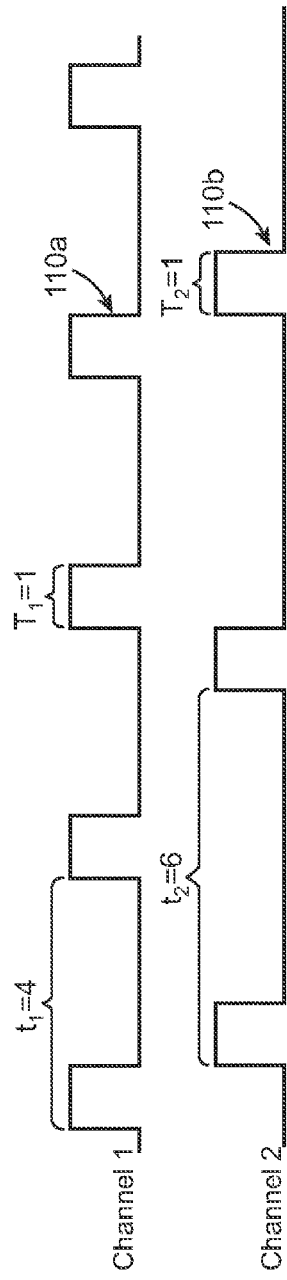
FIG. 9 is a timing diagram illustrating two timing channels that are programmed with a second set of electrical pulsed waveforms by the SCS system of FIG. 2.

In the exemplary case illustrated in FIG. 9, the time period $t_1$ has a unit value of 4, the time period $t_2$ has a unit value of 6, the pulse width $T_1$ has a unit value of 1, and the pulse width $T_2$ has a unit value of 1. In this case, $GCD(t_1, t_2) \geq T_1+T_2$ becomes $GCD(4, 6) \geq 1+1$, which becomes $2 \geq 2$, which is true. Thus, the electrical pulsed waveforms 110a, 110b can be interleaved in a manner without the need to bump pulses to prevent pulse overlap. As such, the CP 18 allows the user to program the timing channels of the IPG 14 with the electrical pulsed waveforms 112, 114.

In the previous cases illustrated in FIGS. 8 and 9, only two timing channels of the IPG 14 are programmed. It should be appreciated that more than two timing channels of the IPG 14 can be programmed. In particular, and with reference to FIG. 10, three timing channels (Channel 1, Channel 2, and Channel 3) of the IPG 14 may potentially be programmed by the CP 18 with three electrical pulsed waveforms 120a, 120b, 120c, respectively. The first electrical pulsed waveform 120a has a time period $t_1$ and a pulse width $T_1$, the second electrical pulsed waveform 120b has a time period $t_2$ and a pulse width $T_2$, and the third electrical pulsed waveform 120c has a time period $t_3$ and a pulse width $T_3$. As with the previous waveforms, these electrical pulsed waveforms 120a, 120b, 120c may be defined in response to an input received by the user interface (mouse 72 or keyboard 74) of the CP 18 in a conventional manner. Stimulation energy can then be delivered from the IPG 14 over the multiple timing channels to in accordance with the programmed pulsed electrical waveforms 120a, 120b, 120c to provide therapy to the patient (e.g., by stimulating different tissue regions of the patient respectively with the programmed pulsed electrical waveforms 120a, 120b, 120c).

As with the previous electrical pulsed waveforms, the CP 18 can determine whether the electrical pulsed waveforms 120a, 120b, 120c can be interleaved in a manner that does not require bumping of any pulses (thereby preventing frequency locking between the timing channels) based on function of the greatest common divisor (GCD) of the time periods $T_1$, $T_2$, $T_3$ and the sum of the pulse widths $T_1$, $T_2$, $T_3$ of the respective electrical pulsed waveforms 120a, 120b, 120c. This function can be generalized as follows: if $GCD(t_1, \ldots, t_x) \geq T_1 + \ldots + T_x$ (where x is the number of electrical pulsed waveforms (or timing channels)), it is determined that the x number of electrical pulsed waveforms can be interleaved without the need to bump pulses to prevent pulse overlap. To this end, the CP 18 computes the GCD of the time periods $t_1, \ldots t_x$ and the sum of the pulse widths $T_1, \ldots T_x$, and allows the timing channels to be programmed with the x number of pulsed electrical waveforms if the GCD of the time periods $t_1, \ldots t_x$ is equal to or greater than the sum of the pulse widths $T_1, \ldots T_x$. The CP 18 may program the timing channels of the IPG 14 simply by interleaving the x number of electrical pulsed waveforms, such that no pulses in the waveforms temporally overlap each other.

Figure 10:
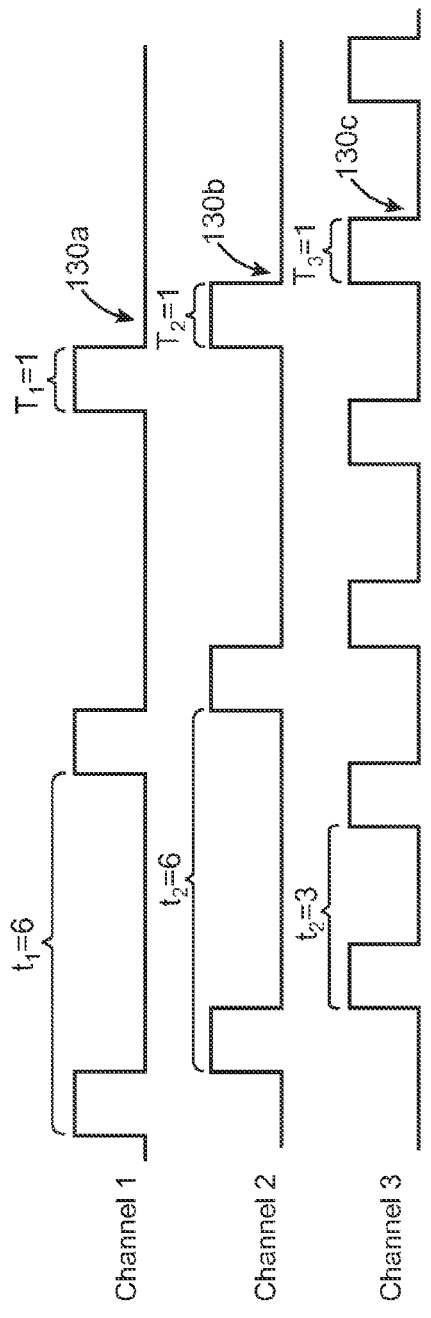
FIG. 10 is a timing diagram illustrating three timing channels that are programmed with a third set of electrical pulsed waveforms by the SCS system of FIG. 2.

In the exemplary case illustrated in FIG. 10, the time period $t_1$ has a unit value of 6, the time period $t_2$ has a unit value of 6, the time period $t_3$ has a unit value of 3, the pulse width $T_1$ has a unit value of 1, the pulse width $T_2$ has a unit value of 1, and the pulse width $T_3$ has a unit value of 1. In this case, $GCD(t_1, \ldots, t_x) \geq T_1 + \ldots +T_x$ becomes $GCD(6,6,3) \geq 1+1+1$, which becomes $3 \geq 3$, which is true. Thus, the electrical pulsed waveforms 120a, 120b, 120c can be interleaved in a manner without the need to bump pulses to prevent pulse overlap. As such, the CP 18 allows the user to program the timing channels of the IPG 14 with the electrical pulsed waveforms 120a, 120b, 120c. It can be appreciated from the example of FIG. 10 that if $t_1=t_2 \neq t_3$; for example, $t_1=t_2=2t_3$ (or $f_1=f_2=\frac{1}{2}f_3$, where f is the frequency), the three electrically pulsed waveforms can be interleaved without requiring the pulses to be bumped to prevent overlap.

Notably, in some circumstances where more than two timing channels are to be used, the GCD criteria may unnecessarily block the use of electrically pulsed waveforms that may otherwise be able to be programmed without requiring bumping of pulses. Thus, there may be exceptions or caveats to the GCD criteria. In one case, if two or more pulsed electrical waveforms can be combined into a single pulsed electrical waveform, then the GCD criteria should be applied to the single pulsed electrical waveform (after combination of the constituent pulsed electrical waveforms) and any other available electrical waveforms.

Figure 11:
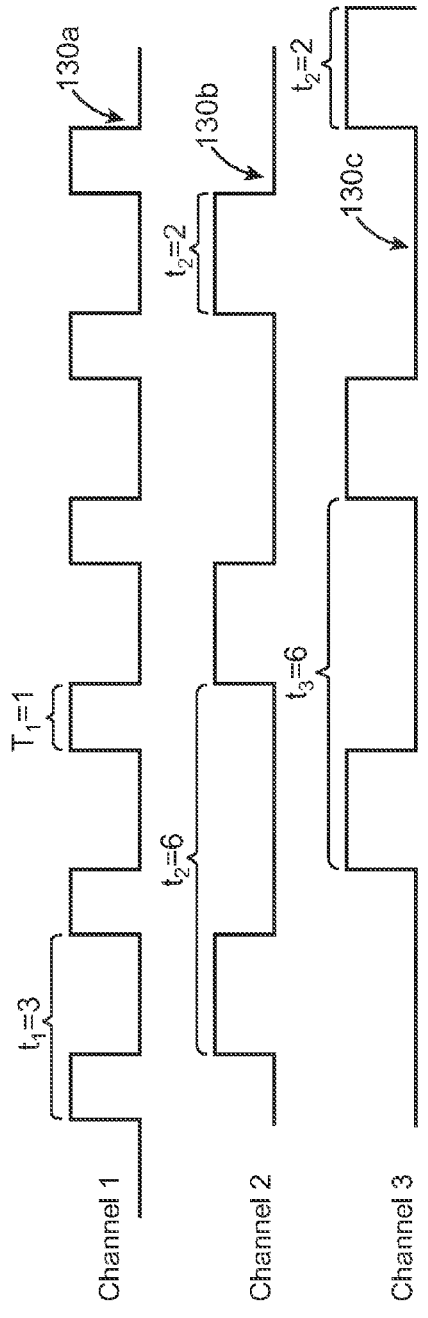
FIG. 11 is a timing diagram illustrating three timing channels that are programmed with a fourth set of electrical pulsed waveforms by the SCS system of FIG. 2.

For example, with reference to FIG. 11, three timing channels of the IPG 14 may potentially be programmed by the CP 18 with three electrical pulsed waveforms 130a, 130b, 130c, respectively. The first electrical pulsed waveform 130a has a time period $T_1$ and a pulse width $T_1$, the second electrical pulsed waveform 130b has a time period $T_2$ and a pulse width $T_2$, and the third electrical pulsed waveform 130c has a time period $T_3$ and a pulse width $T_3$. In this exemplary case, the time period $t_1$ has a unit value of 3, the time period $t_2$ has a unit value of 6, the time period $t_3$ has a unit value of 6, the pulse width $T_1$ has a unit value of 1, the pulse width $T_2$ has a unit value of 2, and the pulse width $T_3$ has a unit value of 2.

In this case, $GCD(t_1, \ldots, t_x) \geq T_1+ \ldots +T_x$ becomes $GCD(3,6,6) \geq 1+1+1$, which becomes $3 \geq 5$, which is false. Thus, without further manipulation of the electrical pulsed waveforms 130a, 130b, 130c, the GCD criteria indicate that the electrical pulsed waveforms 130a, 130b, 130c cannot be interleaved in a manner without the need to bump pulses to prevent pulse overlap. However, if the second and third electrical pulsed waveforms 130b, 130c are interleaved into a single electrical pulsed waveform 130d, as shown in FIG. 12, the resulting time period $t_4$ will be a unit value of 3, and the resulting pulse width $T_4$ will remain at a unit value of 2. In this case, $GCD(t_1, \ldots, t_x) \geq T_1 + \ldots + T_x$ becomes $GCD(3,3) \geq 1+2$, which becomes $3 \geq 3$, which is true. Thus, the electrical pulsed waveforms 130a, 130b, 130c can actually be interleaved in a manner without the need to bump pulses to prevent pulse overlap. As such, the CP 18 allows the user to program the timing channels of the IPG 14 with the electrical pulsed waveforms 130a, 130b, 130c. It should be noted that the combination of channels 2 and 3 into one timing channel need not actually occur in practice; just that it be possible to do so without interrupting it. In other words, if channels 2 and 3 can be created by splitting a different channel, then channels 1, 2, and 3 represent a valid combination.

Thus, the effect of interleaving two or more pulsed electrical waveforms when possible may allow waveforms to be programmed into the IPG 14 that may not otherwise be allowable because the GCD of the periods of all of the pulsed electrical waveforms was not equal to or greater than the sum of the pulse widths of the pulsed electrical waveforms. Although the CP 18 has been described as performing the programming functions described with respect to FIGS. 8-12, the RC 16 can be alternatively used. In this case, the RC 16 is capable of eliminating frequency locking between the timing channels by allowing the user to only program multiple timing channels of the IPG 14 with pulsed electrical waveforms that can be interleaved in a manner that does not require "bumping" of any pulses. In this case, the processor 64 of the RC 16 is used to perform the electrical pulsed waveform definition and computation functions, and the telemetry circuitry 68 of the RC 16 is used to program the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for a neurostimulation device, comprising:
   a user interface configured for receiving an input from a user;
   telemetry circuitry;
   a processor configured for defining a plurality of pulsed electrical waveforms in response to the input from the user, computing the greatest common divisor of the periods of the pulsed electrical waveforms, computing the sum of the pulse widths of the pulsed electrical waveforms, and programming via the telemetry circuitry a plurality of timing channels in the neurostimulation device with the pulsed electrical waveforms if the greatest common divisor is equal to or greater than the sum.

2. The external control device of claim 1, wherein at least two of the plurality of timing channels are programmed with a common electrode.

3. The external control device of claim 1, wherein the plurality of electrical pulsed waveforms have different periods.

4. The external control device of claim 1, wherein the plurality of electrical pulsed waveforms comprises at least three electrical pulsed waveforms.

5. The external control device of claim 1, wherein the electrical pulsed waveforms are defined in response to a user input.

6. The external control device of claim 1, wherein the timing channels are programmed in the neurostimulation device in a manner, such that no pulse temporally overlaps another pulse.

7. The external control device of claim 1, wherein the processor is further configured for interleaving two or more pulsed electrical waveforms into a single pulsed waveform, wherein the plurality of electrical pulsed waveforms includes the single pulsed waveform, and two or more of the timing channels are allowed to be respectively programmed with the two or more pulsed waveforms.

8. The external control device of claim 7, wherein the frequencies of the two or more pulsed electrical waveforms are equal.

9. The external control device of claim 1, wherein the processor is configured for programming the timing channels, such that stimulation energy is delivered from the neurostimulation device in accordance with the programmed pulsed electrical waveforms to provide therapy to a patient.

10. The external control device of claim 9, wherein the processor is configured for programming the timing channels, such that different tissue regions of the patient are stimulated respectively with the delivered stimulation energy.

11. A method for preventing pulse overlap in a multi-channel neurostimulation system using the external device of claim 1, the method comprising:
    defining the plurality of pulsed electrical waveforms;
    computing the greatest common divisor of the periods of the pulsed electrical waveforms;
    computing the sum of the pulse widths of the pulsed electrical waveforms; and
    allowing the plurality of timing channels in the neurostimulation system to be programmed with the pulsed electrical waveforms if the greatest common divisor is equal to or greater than the sum.

12. The method of claim 11, wherein at least two of the plurality of timing channels are programmed with a common electrode.

13. The method of claim 11, wherein the plurality of electrical pulsed waveforms have different periods.

14. The method of claim 11, wherein the timing channels are programmed by an external control device.

15. The method of claim 11, wherein the plurality of electrical pulsed waveforms comprises at least three electrical pulsed waveforms.

16. The method of claim 11, wherein the electrical pulsed waveforms are defined in response to the user input.

17. The method of claim 11, wherein the timing channels are programmed in a manner, such that no pulse temporally overlaps another pulse.

18. The method of claim 11, further comprising interleaving two or more pulsed electrical waveforms into a single pulsed waveform, wherein the plurality of electrical pulsed waveforms includes the single pulsed waveform, and two or more of the timing channels are allowed to be respectively programmed with the two or more pulsed waveforms.

19. The method of claim 18, wherein the periods of the two or more pulsed electrical waveforms are equal.

20. The method of claim 11, further comprising delivering stimulation energy from the neurostimulation system in accordance with the programmed pulsed electrical waveforms to provide therapy to a patient.

21. The method of claim 20, wherein the delivered stimulation energy respectively stimulates different tissue regions of the patient.

* * * * *